United States Patent
Naud et al.

(10) Patent No.: US 7,446,236 B2
(45) Date of Patent: Nov. 4, 2008

(54) CATALYTIC HYDROGENATION OF CARBON-HETEROATOM DOUBLE BONDS

(75) Inventors: Frédéric Maurice Naud, Huningue (FR); Ulrich Pittelkow, Rheinfelden (DE)

(73) Assignee: Solvias AG, Basel (CH)

( * ) Notice: Subject to any disclaimer, the term of this patent is extended or adjusted under 35 U.S.C. 154(b) by 349 days.

(21) Appl. No.: 10/536,883

(22) PCT Filed: Nov. 27, 2003

(86) PCT No.: PCT/EP03/50902

§ 371 (c)(1),
(2), (4) Date: Jun. 1, 2005

(87) PCT Pub. No.: WO2004/050585

PCT Pub. Date: Jun. 17, 2004

(65) Prior Publication Data
US 2006/0106247 A1    May 18, 2006

(30) Foreign Application Priority Data
Dec. 2, 2002  (CH) ................... 2033/02

(51) Int. Cl.
*C07C 27/00* (2006.01)
*C07C 33/18* (2006.01)
(52) U.S. Cl. .................. 568/814; 568/715
(58) Field of Classification Search .............. None
See application file for complete search history.

(56) References Cited

U.S. PATENT DOCUMENTS 5,614,641 A * 3/1997 Genet et al. .......... 549/313
6,476,233 B1 * 11/2002 Zhang .................. 548/238
2003/0199713 A1 10/2003 Berg Van Den et al.

FOREIGN PATENT DOCUMENTS

WO    02/04466    1/2002
WO    02/22526    3/2002

OTHER PUBLICATIONS

Nishibayashi et al., Organometallics 1999, 18, 2291-2293.*
Arikawa et al., Journal of Organometallic Chemistry 572 (1999) 163-168.*
Catalysis in Kirk-Othmer Encyclopedia of Chemical Technology Copyright © 2001 by John Wiley & Sons, Inc. pp. 200-254.*
Ohkuma et al., J. Am. Chem. Soc. 1995, 117, 2675-2676.*
Yasuyoshi Arikawa et al., "Ruthenium (II)-catalyzed asymmetric transfer hydrogenation of ketones using chiral oxazolinylferrocenylphosphines and one of their Ru(II) complex", Journal of Organometallic Chemistry, 572, pp. 163-168, 1999.
Yoshiaki Nishibayashi et al., Extremely High Enantioselective Redox Reaction of Ketones and Alcohols Catalyzed by $RuCl_2(PPh_3)$ (oxazolinylferrocenylphosphine), Organometallics, 18, pp. 2291-2293, 1999.
Kamaluddin Abdur-Rashid, et al., "Ruthenium Dihydride $RuH_2$ $(PPh_3)_2$ ((R, R)-cyclohexyldiamine) and Ruthenium Monohydride $RuHCl(PPh_3)_2$ ((R, R)-cyclohexyldiamine: Active Catalyst and Catalyst Precursor for the Hydrogenation of Ketones and Imines", Organometallics, 19, pp. 2655-2657, 2000.

* cited by examiner

*Primary Examiner*—Karl J Puttlitz
(74) *Attorney, Agent, or Firm*—Wenderoth, Lind & Ponack, L.L.P.

(57) ABSTRACT

Process for catalytically hydrogenating carbon-heteroatom double bonds, in particular for asymmetrically catalytically hydrogenating simple ketones, which includes the step of reacting the substrate with hydrogen in the presence of a hydrogenation catalyst and of a base, characterized in that the hydrogenation catalyst is a 5-coordinate ruthenium complex which in each case has a monophosphine ligand and a bidentate P-N ligand.

18 Claims, No Drawings

CATALYTIC HYDROGENATION OF CARBON-HETEROATOM DOUBLE BONDS

The present invention relates to processes for catalytically hydrogenating carbon-heteroatoms double bonds, in particular for asymmetrically catalytically hydrogenating simple ketones, using nuthenium complexes which each have a monophosphine ligand and a bidentate P-N ligand.

The possibilities for reducing carbon-heteroatom double bonds which are relevant from an industrial viewpoint are firstly transfer hydrogenation and secondly hydrogenation with molecular hydrogen. A prerequisite for both processes is the presence of catalysts for activating the particular reducing agent. The hydrogenation activities achievable in transfer hydrogenations are in principle less promising as a result of circumstances relating to the process (need for large amounts of solvent) than in the hydrogenation with molecular hydrogen. Since, however, molecular hydrogen is significantly more difficult to activate than an alcohol, which serves as the reducing agent in the transfer hydrogenation, some catalyst systems for transfer hydrogenation have in recent times become known, but only comparatively few catalyst systems for hydrogenation with hydrogen. In particular, only very few catalyst systems are known hitherto for substrates in the form of simple ketones. Simple ketones are those ketones which have no functional groups, or more precisely no heteroatoms, in the relative vicinity of the carbonyl group, as is the case, for example, in α-keto esters and amides, β-keto esters or amino, hydroxy and phenylthio ketones.

The first example of an efficient catalyst system for the catalytic $H_2$ hydrogenation of nonfunctionalized ketones is described by R. Noyori and T. Ohkuma in Angew. Chem. Int Ed. 2001, 40, 40ff. This is a process for asymmetrically hydrogenating simple carbonyl compounds with hydrogen gas under a pressure of up to 50 bar using a homogeneous Ru(II) complex of the $Cl_2Ru(PR_3)_3$ type, in the presence of isopropanol, of a molar excess of a base, and of a nitrogen-containing organic compound in the form of a primary, secondary or tertiary monoamine, or preferably a diamine. The catalytic precursors obtained are 6-coordinate $(Cl)_2Ru(phosphine)_2(N^\wedge N)$ and $(Cl)_2Ru(P^\wedge P)(N^\wedge N)$ complexes. The efficient action of these complexes is attributed to the properties of the amine ligand which, during the catalysis process, functions on the one hand as a hydrogen atom donor for the reduction of the substrate and on the other hand as a hydrogen atom acceptor for the activation of the molecular hydrogen (R. Noyori and T. Ohkuma in Angew. Chem. Int. Ed. 2001, 40, 40ff and R. H. Morris, Organometallics 2000, 19, 2655).

The second, later example of a further class of catalysts which enable the hydrogenation of simple ketones is described in WO 02/22526 A2. This describes the preparation of 6-coordinate ruthenium complexes having two bidentate ligands but no amine ligands. The two bidentate ligands are either an N^P ligand in combination with a P^P ligand, or alternatively two N^P ligands.

It is noticeable in the aforementioned examples that, although the complexes have different phosphorus and nitrogen ligands, there are no differences with regard to the coordination sphere on the central ruthenium atom, since the complexes mentioned always have 6-fold coordination. The nature of the ligand sphere around the particular central atom of a complex is known to exert a great influence on the possible activity of the complex.

It has now been found that suitable catalyst precursors for the catalytic hydrogenation of simple ketones with hydrogen are also 5-coordinate ruthenium complexes whose ligands are one monophosphine and one bidentate P^N ligand.

The present invention therefore provides a process for hydrogenating a substrate containing a carbon-heteroatom double bond, which includes the step of reacting the substrate with hydrogen in the presence of a hydrogenation catalyst and of a base, characterized in that the hydrogenation catalyst is a transition metal complex of the formula (I)

$$[X\ Y\ Ru\ (P\ R_1R_2R_3)\ (P\text{-}Z\text{-}N)] \quad (I)$$

where

X, Y are each independently a hydrogen atom, halogen atom, $C_{1-8}$alkoxy or $C_{1-8}$acyloxy group, or a coordinatively bound organic solvent molecule containing at least one heteroatom having at least one free electron pair, for example in the form of (cyclo)alkyl/aryloxy, -thio or -amino groups, in which case the charge of the resulting cationic complex is balanced by an anion, for example $CN^-$, $OCN^-$, $PF_6^-$ or $F_3C\text{—}SO_2O^-$, $R_1$, $R_2$, $R_3$ are each independently an alkyl, alkyloxy, alkylthio, dialkyamino, cycloalkyl, cycloalkyloxy, cycloalkylthio, dicycloalkylamino, aryl, aryloxy, arylthio or diarylamino group, optionally substituted by 1,2 or 3 radicals which are each independently selected from $C_{1-4}$alkyl groups and $C_{1-4}$alkoxy groups, or one of the $R_1$, $R_2$, $R_3$ radicals is as defined above and the remaining 2 radicals which, linked either via an oxygen bridge or directly to the phosphorus atom, form, including the phosphorus atom, a 4- to 8-membered, optionally substituted ring, P-Z-N is a bidentate ligand which contains an $sp^2$-hybridized nitrogen atom and is of the formula (II)

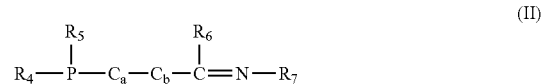

$$R_4\text{—}P\overset{\underset{\displaystyle |}{R_5}}{\phantom{X}}\text{—}C_a\text{—}C_b\text{—}\overset{\underset{\displaystyle |}{R_6}}{C}\text{=}N\text{—}R_7 \quad (II)$$

where $R_4$, $R_5$ are each independently a linear, branched or cyclic $C_{1-8}$alkyl or $C_{2-8}$alkenyl group, optionally substituted; $C_{6-18}$aryl, $C_{3-18}$heteroaryl, $C_{3-8}$cycloalkyl, $(C_{1-8}\text{Alkyl})_{1-3}$-(Hetero)Aryl, optionally substituted, whereby possible substituents are halogen, organohalogen group, $O(C_{1-8})$alkyl, $N(C_{1-8}\text{alkyl})_2$; or $R_4$ and $R_5$ together are a saturated or aromatic ring composed of 5 to 10 atoms including the phosphorus atom, $C_a$, $C_b$ are each a part of an aromatic, optionally substituted (hetero)aryl having at least 6 $\pi$-electrons, $R_6$ is a hydrogen atom, a linear, branched or cyclic $C_{1-10}$alkyl or $C_{2-10}$alkenyl group, optionally substituted, an aromatic ring, optionally substituted, a —$OR_{6'}$ or —$NR_{6'}R_{6''}$ radical, where $R_{6'}$ and $R_{6''}$ are as defined for $R_6$, $R_7$ is a hydrogen atom, a linear, branched or cyclic $C_{1-10}$alkyl or $C_{2-20}$alkenyl group, or an $R_{7'}CO$ or $R_{7'}SO_2$ radical where $R_{7'}$ is a $C_{1-8}$alkyl or aryl group, or $R_6$ and $R_7$ together are an unsaturated (hetero)cycle composed of 5 to 10, optionally substituted ring atoms, including the carbon and the nitrogen atom to which $R_6$ and $R_7$ are bonded, and optionally including further heteroatoms.

The aforementioned process is suitable for highly selectively hydrogenating ketones to prepare the corresponding optically pure alcohols.

Suitable substrates are ketones of the general formula (S):

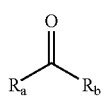

(S)

When $R_a$ and $R_b$ are different, these are prochiral ketones and the hydrogenation catalyzed by the complexes according to the invention to the corresponding alcohols is enantioselective. The enantiomeric excess is more than 80% (ee), preferably more than 90%, in particular more than 95%.

With regard to the Ra and Rb radicals, there are in principle no restrictions. The radicals are each independently a hydrogen atom, straight-chain or branched alkyl, monocyclic or polycyclic aryl, (hetero)aryl or (hetero)aralkyl groups, and all groups may in turn have further groups such as alkyl, (hetero)aryl or (hetero)aralkyl groups. The carbonyl function to be reduced may also be incorporated into a mono- or polycyclic ring structure. Although a feature of the process according to the invention is that nonfunctionalized ketones in particular can also be hydrogenated, the $R_a$ and $R_b$ radicals may each independently have functional groups. The only restriction for these is that they do not react with the catalyst to destroy it. Possible substituents of the $R_a$ and $R_b$ radicals and in the formula (S) are Hal, $OR^x$, $NR_2^x$ or $R^x$, where $R^x$ is H, or a linear, branched or cyclic $C_{1-10}$alkyl or $C_{2-10}$alkenyl group.

Preferred substrates are prochiral ketones of the formula (S), where $R_a$ and $R_b$ are each independently a hydrogen atom, a cyclic, linear or branched $C_{1-8}$alkyl or $C_{2-8}$alkenyl group, or an monocyclic or polycyclic aryl or heteroaryl group, optionally substituted by linear or branched $C_{1-8}$alkyl-, $C_{1-8}$alkoxy groups or halogen atoms.

Examples of substrates of the formula (S) include in particular monocyclic or polycyclic aryl ketones or heteroaryl ketones, optionally substituted by linear or branched $C_{1-8}$alkyl-, $C_{1-8}$alkoxy groups or halogen atoms.

The aforementioned process is also suitable for hydrogenating substrates containing a C=N double bond corresponding to the general formula (O):

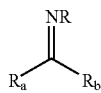

(O)

When $R_a$ and $R_b$ are different, these are prochiral imines and the hydrogenation catalysed by the complexes according to the invention to the corresponding amines is enantioselective. The enantiomeric excess is more than 80% (ee), preferably more than 90%, in particular more than 95%.

With regard to the $R_a$ and $R_b$ radicals, there are in principle no restrictions. The possible $R_a$ and $R_b$ radicals correspond to those specified under the formula (S). R in the formula (O) may be, for example, an H, OR, SR, $P(O)R_2$ radical where R may in each case be a linear or branched $C_{1-8}$alkyl or alkenyl group, optionally substituted, or an aromatic ring, optionally substituted. Possible substituents of the NR radical are Hal, $OR^x$, $NR_2^x$ or $R^x$ where $R^x$ is H, or a linear, branched or cyclic $C_{1-10}$alkyl or alkenyl group.

The process according to the invention for hydrogenating a substrate containing a carbon-heteroatom double bond is characterized in that the hydrogenation catalyst is a transition metal complex of the general formula (I):

$$[X\,Y\,Ru\,(P\,R_1R_2R_3)\,(P\text{-}Z\text{-}N)] \tag{I}$$

In the formula (I), X and Y are preferably each independently a hydrogen atom or a halogen atom, preferably a chlorine atom. Particular preference is given to X and Y each being a chlorine atom.

Monophosphines $P\,R_1R_2\,R_3$ used with preference in the complexes of the formula (I) according to the invention are those in which the $R_1$, $R_2$, $R_3$ radicals are each independently a $C_{1-4}$alkyl group, $C_{5-6}$cycloalkyl group, or a phenyl group, optionally substituted by 1,2 or 3 radicals which are each independently selected from $C_{1-4}$alkyl groups and $C_{1-4}$alkoxy groups. They are preferably methyl, ethyl, n-propyl, i-propyl, n-butyl, i-butyl, cyclopentyl, cyclohexyl or phenyl, o- or p-tolyl, p-isopropylphenyl or mesityl. Particularly preferred monophosphines are triphenylphosphine, tri-$C_{1-4}$alkylphosphine, tritolylphosphine or trimesitylphosphine.

The P-Z-N moiety in the complexes of the formula (I) according to the invention is a bidentate ligand which contains one nitrogen atom and is of the formula (II):

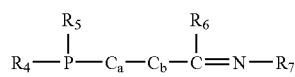

(II)

In the formula (II), $R_4$, $R_5$ are each independently preferably $C_{1-4}$alkyl, preferably each independently methyl, ethyl, n-propyl, i-propyl, n-butyl, i-butyl. $R_4$, $R_5$ are each independently more preferably $C_{6-18}$aryl, $C_{3-18}$heteroaryl, $C_{3-8}$cycloalkyl, $(C_{1-8}Alkyl)_{1-3}$-(Hetero)Aryl, optionally substituted, whereby possible substituents are halogen, organohalogen group, $O(C_{1-8})$alkyl, $N(C_{1-8}alkyl)_2$; or $R_4$ and $R_5$ together are a saturated or aromatic ring composed of 5 to 10 atoms including the phosphorus atom.

When $R_4$ and $R_5$ together form a saturated or aromatic ring including the phosphorus atom, $R_4$ and $R_5$ together are preferable n-butylene, n-pentylene or 2,2'-biphenylene.

In the formula (II), $C_a$, $C_b$ together form part of an aromatic, optionally substituted (hetero)aryl having 6 or more than 6π-electrons. The basic aromatic structures may be fused benzene in the form of polycyclic aromatics such as naphthalene, anthracene, phenanthrene or heteroaromatics such as quinoline or isoquinoline, or a cyclopentadienide ion as a ligand of a metallocene. It is preferably a pure 6 s-electron system in the form of in each case optionally substituted benzene, or a 6π- or 10π-electron heteroaromatic system.

In the formula (II), $R_6$ and $R_7$ are preferably each independently a hydrogen atom, a linear or branched $C_{1-4}$alkyl group, optionally substituted, or an aromatic ring, optionally substituted, or $R_6$ and $R_7$ together with particular preference form an unsaturated heterocycle composed of 5 to 10, optionally substituted ring atoms, including the carbon and the nitrogen atom to which $R_6$ and $R_7$ are bonded, and optionally including further heteroatoms.

Preferred ligands of the formula (II) are firstly ligands of the general formula (IIIa),

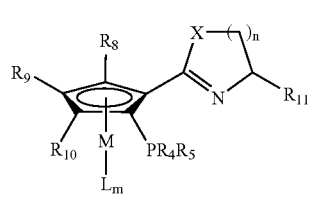

(IIIa)

where
n=1 or 2, preferably 1,
m, depending on M, is the number of free coordination sites on the central atom M,
M Cr, Mo, Fe, Ru, Os, Mn or Re, preferably Re,
X=O, S or N, preferably O,
L are each independently mono- or polydentate ligands to fill the free coordination sites on the central atom M, such as $P(C_{6-18}aryl)_3$, $P(C_{6-18}alkyl)_3$, $H_2NCH_2CH_2NH_2$, $(C_{6-18}aryl)_2PCH_2CH_2P(C_{6-18}aryl)_2$ or preferably CO,
$R_4$, $R_5$ are each radicals corresponding to the definition given under formula (II),
$R_{11}$ is a $C_{2-8}$alkoxyalkyl, $C_{7-19}$aralkyl, $C_{3-18}$heteroaryl, $C_{4-19}$heteroaralkyl,
$(C_{1-8}alkyl)_{1-3}$-$C_{6-18}$(hetero)aryl, $(C_{1-8}alkyl)_{1-3}$-$C_{6-18}$cycloalkyl, $C_{3-8}$cycloalkyl,
$C_{3-8}$cycloalkyl-$C_{1-8}$alkyl radical, or preferably a $C_{1-8}$alkyl, $C_{6-18}$aryl radical, and the radicals mentioned may be substituted by one or more heteroatoms such as Hal, Si, N, O, P, S, or the radicals may have one or more heteroatoms such as Si, N, O, P, S in their carbon framework,
$R_{8,9,10}$ are each independently a $C_{1-8}$alkyl, $C_{2-8}$alkoxyalkyl, $C_{6-18}$aryl, $C_{7-19}$aralkyl,
$C_{3-18}$heteroaryl, $C_{4-19}$heteroaralkyl, $(C_{1-18}alkyl)_{1-3}$-$C_{6-18}$(hetero)aryl, $C_{3-8}$cycloalkyl,
$(C_{1-8}alkyl)_{1-3}$-$C_{6-18}$cycloalkyl, $C_{3-8}$cycloalkyl-$C_{1-8}$alkyl radical, or preferably H, and the radicals mentioned may be substituted by one or more heteroatoms such as Hal, Si, N, O, P, S, or the radicals may have one or more heteroatoms such as Si, N, O, P, S in their carbon framework.

Preferred ligands of the formula (II) are also ligands of the formula (IIIb)

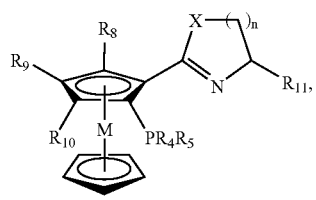

(IIIb)

where
n=1 or 2, preferably 1,
M=Fe, Ru, Os, preferably Fe,
X=O, S or N, preferably O,
$R_4$, $R_5$ are each radicals corresponding to the definition given under formula (II),
$R_{11}$ is a $C_{2-8}$alkoxyalkyl, $C_{7-19}$aralkyl, $C_{3-18}$heteroaryl, $C_{4-19}$heteroaralkyl,
$(C_{1-8}alkyl)_{1-3}$-$C_{6-18}$(hetero)aryl, $(C_{1-8}alkyl)_{1-3}$-$C_{6-18}$cycloalkyl, $C_{3-18}$cycloalkyl,
$C_{3-8}$cycloalkyl-$C_{1-18}$alkyl radical, or preferably $C_{1-18}$alkyl, $C_{6-18}$aryl radical, in particular i-propyl, and the radicals mentioned may be substituted by one or more heteroatoms such as Hal, Si, N, O, P, S, or the radicals may have one or more heteroatoms such as Si, N, O, P, S in their carbon framework,
$R_{8,9,10}$ are each independently a $C_{1-8}$alkyl, $C_{2-8}$alkoxyalkyl, $C_{6-18}$aryl, $C_{7-19}$aralkyl,
$C_{3-18}$heteroaryl, $C_{4-19}$heteroaralkyl, $(C_{1-8}alkyl)_{1-3}$-$C_{6-18}$(hetero)aryl, $C_{3-8}$cycloalkyl,
$(C_{1-8}alkyl)_{1-3}$-$C_{6-18}$cycloalkyl, $C_{3-8}$cycloalkyl-$C_{1-8}$alkyl radical, or preferably H, and the radicals mentioned may be substituted by one or more heteroatoms such as Hal, Si, N, O, P, S, or the radicals may have one or more heteroatoms such as Si, N, O, P, S in their carbon framework, and the lower cyclopentadienide ligand in the formula may, with respect to the abovementioned possible substitution pattern for the upper cyclopentadienide ligand, be correspondingly substituted with regard to the possible $PR_{4,5}$ and $R_{8,9,10}$ radicals.

As already mentioned, $C_a$, $C_b$ in the formula (II) together form part of an aromatic, optionally substituted (hetero)aryl having 6 or more than 6 π-electrons, which is preferably a pure 6 π-electron system in the form of in each case optionally substituted benzene, or is a 6 π- or 10 π-electron heteroaromatic system. Preferred ligands of the formula (II) are therefore also ligands of the general formulae (IV) and (V):

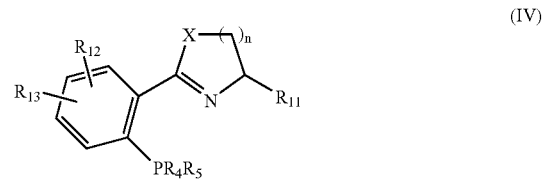

(IV)

where
n=1 or 2, preferably 1,
X=O, S or N, preferably O,
$R_4$, $R_5$ are each radicals corresponding to the definition given under formula (II),
$R_{11}$ is a $C_{2-8}$alkoxyalkyl, $C_{7-19}$aralkyl, $C_{3-18}$heteroaryl, $C_{4-19}$heteroaralkyl,
$(C_{1-8}alkyl)_{1-3}$-$C_{6-18}$(hetero)aryl, $(C_{1-8}alkyl)_{1-3}$-$C_{6-18}$cycloalkyl, $C_{3-8}$cycloalkyl,
$C_{3-8}$cycloalkyl-$C_{1-18}$alkyl radical, or preferably $C_{1-8}$alkyl, $C_{6-18}$aryl radical, in particular i-propyl, and the radicals mentioned may be substituted by one or more heteroatoms such as Hal, Si, N, O, P, S, or the radicals may have one or more heteroatoms such as Si, N, O, P, S in their carbon framework,
$R_{12}$, $R_{13}$ are each independently a $C_{1-4}$alkyl, $C_{1-4}$alkoxy radical, or preferably H, or are together a fused cycloalkyl or aryl ring.

Preferred ligands of the formula (II) are also ligands of the general formula (V)

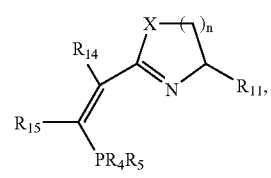

(V)

where
n, X, $R_4$, $R_5$ and $R_{11}$, are each as defined under formula (IV), and $R_{14}$ and $R_{15}$ together are a 6 π- or 10 π-electron heteroaromatic system, optionally substituted by linear or branched $C_{1-8}$alkyl radicals, and possible heteroatoms are N, O, or S.

Particularly preferred ligands of the general formula (IIIb) correspond to the following ligands A to G:

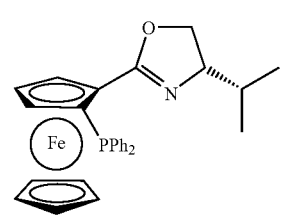

A

-continued

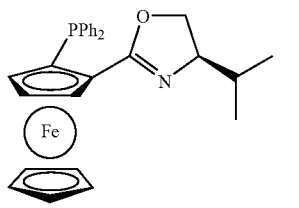

B

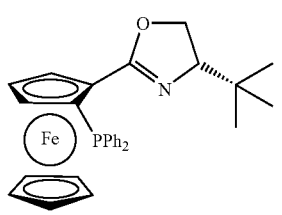

C

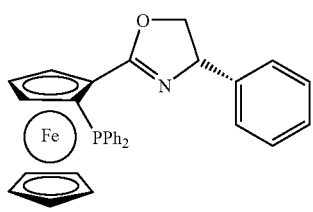

D

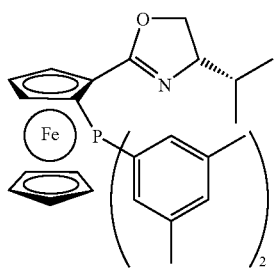

E

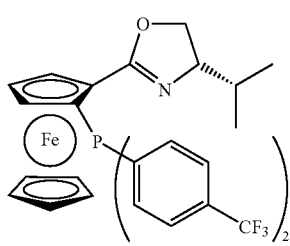

F

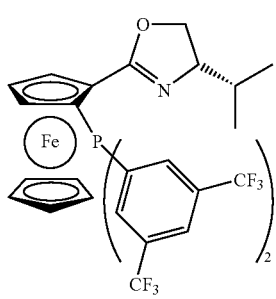

G

A particularly preferred ligand of the general formula (IV) corresponds to the formula J:

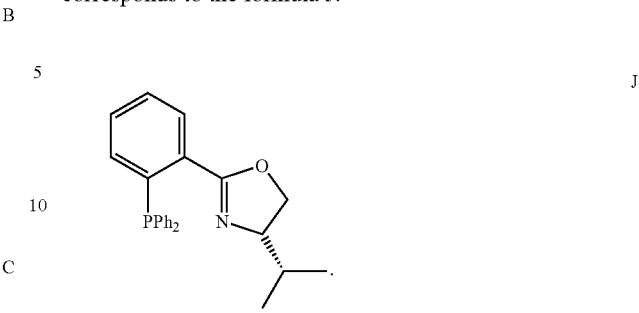

J

Particularly preferred ligands of the general formula (V) correspond to the formulae H, I and K:

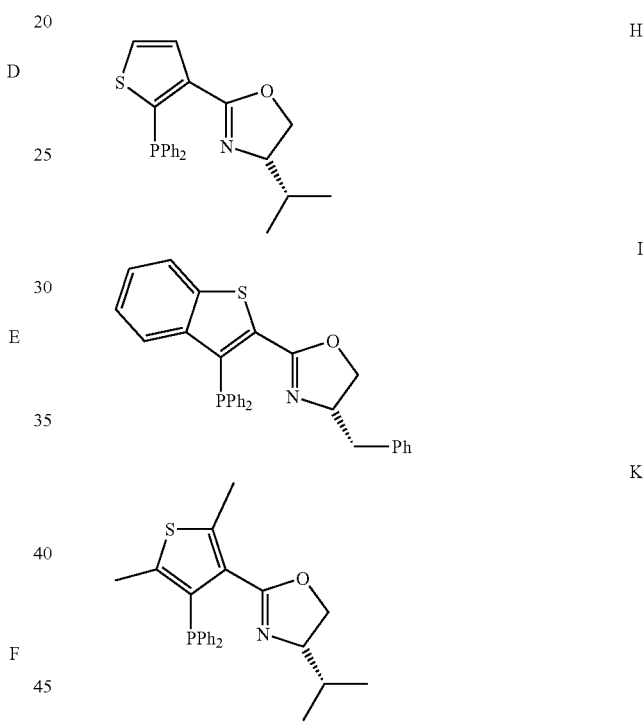

H

I

K

Linear or branched $C_{1-8}$alkyls are to be regarded as being methyl, ethyl, n-propyl, isopropyl, n-butyl, isobutyl, sec-butyl, tert-butyl, pentyl, hexyl, heptyl or octyl, including all of their structural isomers.

$C_{2-8}$Alkoxyalkyls mean radicals in which the alkyl chain is interrupted by at least one oxygen function, although two oxygen atoms may not be joined together. The number of carbon atoms indicates the total number of carbon atoms present in the radical. All structural isomers are included.

$C_{3-8}$Cycloalkyl radical refers to cyclopropyl, cyclobutyl, cyclopentyl, cyclohexyl and cycloheptyl radicals, etc. Cycloalkyl radicals substituted by heteroatoms are preferably, for example, 1-, 2-, 3-, 4-piperidyl, 1-, 2-, 3-pyrrolidinyl, 2-, 3-tetrahydrofuryl, 2-, 3-, 4-morpholinyl.

A $C_{3-8}$cycloalkyl-$C_{1-8}$alkyl radical denotes a cycloalkyl radical as illustrated above which is linked to the molecule via an alkyl radical as specified above.

A $C_{6-18}$aryl radical refers to an aromabic radical having 6 to 18 carbon atoms. These include in particular compounds such as phenyl, naphthyl, anthryl, phenanthryl, biphenyl radicals.

A $C_{7-19}$aralkyl radical is a $C_{6-18}$aryl radical linked to the molecule via a $C_{1-8}$alkyl radical. In the context of the invention, a $C_{3-18}$heteroaryl radical denotes a five-, six- or seven-membered aromatic ring system composed of 3 to 18 carbon atoms which has heteroatoms in the ring, for example nitrogen, oxygen or sulphur. Such heteroaromabcs are regarded as being in particular radicals such as 1-, 2-, 3-furyl, 1-, 2-, 3-pyrrolyl, 1-, 2-, 3-thienyl, 2-, 3-, 4-pyridyl, 2-, 3-, 4-, 5-, 6-, 7-indolyl, 3-, 4-, 5-pyrazolyl, 2-,4-, 5-imidazolyl, acridinyl, quinolinyl, phenanthridinyl, 2-, 4-, 5-, 6-pyrimidinyl.

A $C_{4-19}$heteroaralkyl refers to a heteroaromatic system as defined above corresponding to the $C_{7-19}$aralkyl radical.

Hal is fluorine, chlorine, bromine, iodine, preferably chlorine. Organohalogen compounds is the collective term used for compounds containing, in addition to carbon, elements of the halogen group, including fluorine, chlorine, bromine and iodine. An example is the $CF_3$ group.

The specific bidentate P-Z-N ligands of the general formula (II) and their preparation are known in principle from the literature. Some references are cited in the experimental section. The transition metal complexes of the general formula (I) may if desired be prepared "in situ" in the reaction mixture which contains the substrate to be hydrogenated, or may initially be isolated before a hydrogenation. The preparative process of the complexes is in principle the same. When preparing the complexes, the P-Z-N ligand is in principle introduced stoichiometrically.

The transition metal complexes of the general formula (I) may advantageously be used to hydrogenate simple ketones in particular. Indeed even simple ketones which do not contain a coordinating heteroatom nearby the carbonyl group can be hydrogenated with high activity and enantioselectivity. In the light of the high activity of the catalyst, reduction of non prochiral ketone to make achiral alcohol can be also of practical interest for cost efficient synthesis of secondary alcohol.

The hydrogenation is typically effected in compositions comprising a complex of the formula (I), the substrate, a base and optionally a solvent. Hydrogen is then injected to this composition under the desired pressure and at the desired temperature. The hydrogenation conditions to be selected follow in principle from the customary conditions and essential process parameters such as pressure, temperature, concentration of substrate and catalyst, solvent, bases, which are known from the prior art. The process conditions outlined below have only exemplary character The concentration range of the complexes based on the substrate may vary widely. In general, based on the substrate, between 0.1 and 50 000 ppm are used. This corresponds to a substrate/complex rabo (S/C) of $10^7$ to 20.

The bases used may be any inorganic or organic bases customarily used in hydrogenabon. Mention is made only of alkali metal and alkaline earth metal hydroxides, alkoxides and carbonates, and quaternary ammonium salts. Preference is given to using KOH, KOMe, KOiPr, KOtBu, UOH, LiOMe, LiOiPr, NaOH, NaOMe or NaOiPr. The bases may be used in solid form or dissolved in alcohol or preferably in water, for example KOtBu/tBuOH (1 molar) or NaOH/H$_2$O (1 molar). In addition, the bases used may be used within a large concentration range. In molar equivalents of base, expressed relative to the metal complex (B/M), the ratio may be about 0.5 to 50 000, preferably 2 to 10 000.

The process according to the invention can be carried out without or in the presence of an inert solvent. Suitable solvents are, for example, aliphatic, cycloaliphatic and aromatic hydrocarbons (pentane, hexane, petroleum ether, cyclohexane, methylcyclohexane, benzene, toluene, xylene), aliphatic halohydrocarbons (methylene chloride, chloroform, di- and tetrachloroethane), nitriles (acetonitrile, propionitrile, benzonitrile), ethers (diethyl ether, dibutyl ether, t-butyl methyl ether, ethylene glycol dimethyl ether, ethylene glycol diethyl ether, diethylene glycol dimethyl ether, tetrahydrofuran or dioxane), ketones (acetone, methyl isobutyl ketone), carboxylic esters and lactones (ethyl or methyl acetate, valerolactone), N-substituted lactams (N-methylpyrrolidone), carboxamides (dimethylacetamide, dimethylformamide), acyclic ureas (tetramethylurea) or cyclic ureas (dimethylimidazolidinone), and sulphoxides and sulphones (dimethyl sulphoxide, dimethyl sulphone, tetramethylene sulphoxide, tetramethylene sulphone) and alcohols (methanol, ethanol, propanol, butanol, ethylene glycol monoethyl ether, diethylene glycol monomethyl ether) and water. The solvents may be used alone or in a mixture of at least two solvents. Preference is given to using toluene.

The hydrogenation process according to the invention may be carried out at typical pressures of $10 \times 10^3$ to $10 \times 10^5$ Pa (1 to 100 bar). Advantageously, $20 \times 10^4$ to $85 \times 10^4$ (20 to 85 bar), in particular $80 \times 10^4$ Pa (80 bar), are used.

The hydrogenation reactions are typically carried out at standard room temperature, i.e. between about 20° C. and 35° C. However, depending mainly on the solvents used, or more specifically the solubility behaviour of the reactants used, the selected temperature may also be between about 0° C. and 100° C.

The nonlimiting examples which follow illustrate the invention in detail:

EXAMPLES

The substrates used were:

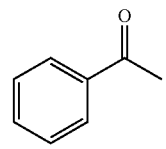

1

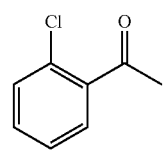

2

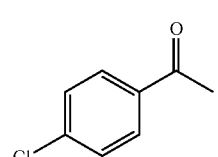

3

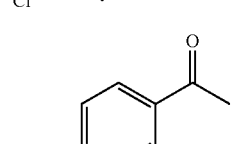

4

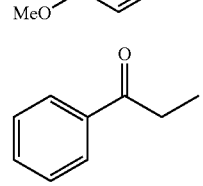

5

-continued
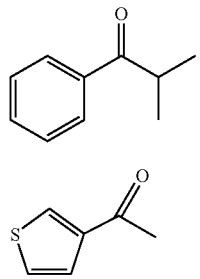
Ligands used were:
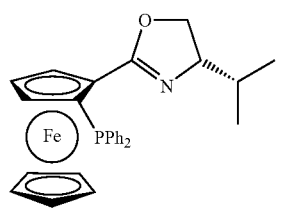
A
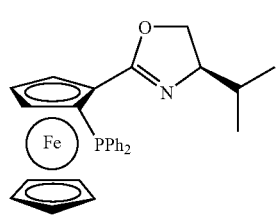
B
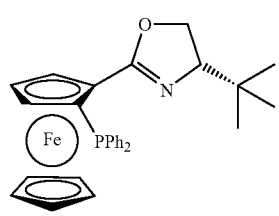
C
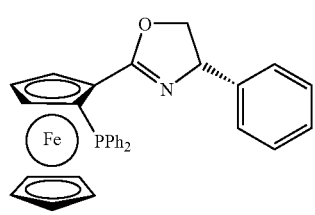
D
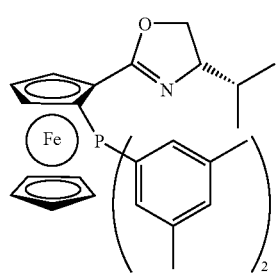
E
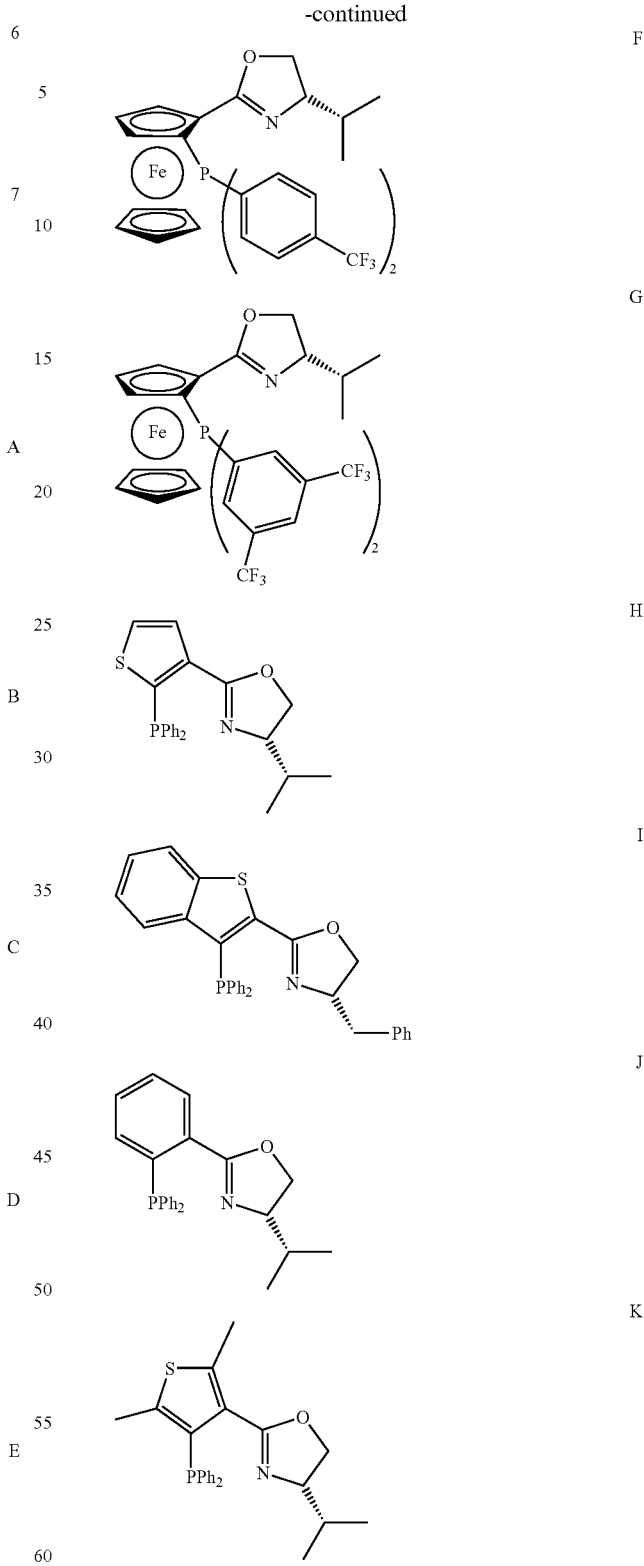
The ligands A to D were prepared in accordance with reference (1). The ligands E to G were prepared in accordance with the experimental section which follows. The ligands H, I and K were prepared in accordance with reference (2). The ligand J is commercially available from Strem.

The catalyst [RuCl$_2$(PPh$_3$) (A)] is prepared in accordance with reference (3).

(1) S. Uemura et al., *J. Organometallic Chem.*, 1999, 572, 163

(2) L. Tietze et al., *Synlett* 2002, 12, 2083.

(3) S. Uemura, M. Hidai et al., *Organometallics* 1999, 18, 2291;

Preparation of Ligands E, F and G:

Ligand E:

A 250 ml 3-necked flask is charged with ferrocene-oxazoline precursor (2.0 g, 6.8 mmol), prepared in accordance with the abovementioned reference (3), TMEDA (1.2 ml, 8.2 mmol) and 70 ml of diethyl ether. The solution is cooled to −70° C. and it becomes yellow and cloudy. A syringe is used to slowly (over about 10 min) add n-BuLi (1.6 M hexane, 5.5 ml, 8.8 mmol), while keeping the temperature of the reaction mixture below −65° C. After the addition, the mixture is stirred at −70° C. for 2 hours, the dry ice bath is removed and the reaction solution is stirred at 0-5° C. for a further 15 min. A syringe is now used to slowly (over about 10 min) add 3.5 9 of PCl(xylyl)$_2$, 12.6 mmol. The now dark orange-coloured solution is stirred at room temperature for about 15 min, and 50 ml of diethyl ether are subsequently added. The reaction is now stopped by adding 30 ml of a saturated NaHCO$_3$ solution. Extraction is effected 3 times with 50 ml each time of EtOAc, and the combined organic phases are dried over Na$_2$SO$_4$. After removing the solvents on a rotary evaporator, 3.3 g of an orange-brown-coloured oil are obtained. This is purified by column chromatography (240 g of SiO$_2$, 4:1 heptane/ethyl acetate) to obtain 1.5 g of a pure orange-coloured crystalline product.

Yield: 1.5 g, 46% of theory).

$^1$H NMR (300.13 MHz, C$_6$D$_6$): δ0.95 (d, 3 H, HCH$_3$), 1.05 (d, 3 H, HCH$_3$), 1.65 (m, 1 H, CH(CH$_3$)$_2$), 2.1 (s, 1 H, Ar—CH$_3$), 2.2 (s, 1 H, Ar—CH$_3$), 3.80 (m, 2 H, O—CH$_2$—CH—), 3.90 (m, 1 H, O—CH$_2$—CH—), 3.95 (m, 1 H, Cp-H), 4.10 (m, 1 H, Cp-H), 4.30 (s, 5 H, Cp), 5.20 (m, 1 H, Cp-H), 6.80 (br. s, 1 H, Ar—H), 6.90 (br. s, 1 H, Ar—H), 7.35 (m, 2 H, Ar—H), 7.60 (m, 2 H, Ar—H). $^{31}$P{$^1$H} (121.5 MHz, C$_6$D$_6$): δ−16.4.

Ligand F

A 250 ml 3-necked flask is charged with ferrocene-oxazoline precursor (2.0 g, 6.8 mmol), prepared in accordance with the abovementioned reference (3), TMEDA (1.2 ml, 8.2 mmol) and 60 ml of diethyl ether. The solution is cooled to −70° C. and it becomes yellow. A syringe is used to slowly (over about 10 min) add n-BuLi (1.6 M hexane, 5.5 ml, 8.8 mmol), while keeping the temperature of the reaction mixture below −65° C. After the addition, the mixture is stirred at −70° C. for 3 hours, the dry ice bath is removed and the reaction solution is stirred at 0-5° C. for a further 15 min. A syringe is now used to slowly (over about 10 min) add 1.8 g of PCl(p-CF$_3$-aryl))$_2$, 6 mmol. The now dark orange-coloured solution is stirred at room temperature for about 60 min, and 50 ml of diethyl ether are subsequently added. The reaction is now stopped by adding 30 ml of a saturated NaHCO$_3$ solution. Extraction is effected 3 times with 50 ml each time of EtOAc, and the combined organic phases are dried over Na$_2$SO$_4$. After removing the solvent on a rotary evaporator, a brown oil is obtained. A small amount of ethyl acetate is added so that the oil just dissolves. Heptane is now added slowly, which leads to the precipitation of an orange-coloured precipitate (1 g) which is removed by means of a fruit. After removing the solvents in the filtrate on a rotary evaporator, a brown-coloured oil is obtained. This is purified by column chromatog raphy (120 g of SiO$_2$, 4:1 heptane/ethyl acetate) to obtain 1.4 g of a pure orange-coloured crystalline product.

Yield: 2.4 g, 65% of theory.

$^1$H NMR (300.13 MHz, C$_6$D$_6$): δ0.95 (d, 3 H, HCH$_3$), 1.05 (d, 3 H, HCH$_3$), 1.65 (m, 1 H, CH(CH$_3$)$_2$), 3.50 (broad s, 1 H, Cp-H), 3.75 (m, 2 H, O—CH$_2$—CH—), 3.95 (m, 1 H, O—CH$_2$—CH—), 4.10 (1 H, Cp-H), 4.20 (s, 5 H, Cp), 5.10 (broad s, 1 H, Cp-H), 7.20-7.50 (m, aryl-H, 8 H). $^{31}$P{$^1$H} (121.5 MHz, CDCl$_3$): δ−16.9.

Ligand G:

A 250 ml 3-necked flask is charged with ferrocene-oxazoline precursor (2.97 g, 10 mmol), prepared in accordance with the abovementioned reference (3), TMEDA (1.8 ml, 12.0 mmol) and 60 ml of diethyl ether. The solution is cooled to −70° C. and it becomes yellow and cloudy. A syringe is used to slowly (over about 10 min) add n-BuLi (1.6 M hexane, 8.6 ml, 13.6 mmol), while keeping the temperature of the reaction mixture below −65° C. After the addition, the mixture is stirred at −70° C. for 2 hours, the dry ice bath is removed and the reaction solution is stirred at 0-5° C. for a further 15 min. A syringe is now used to slowly (over about 10 min) add 6.0 g of PCl(3,5-CF$_3$-aryl)$_2$, 12.2 mmol. The now dark orange-coloured solution is stirred at room temperature for about 15 min, and 50 ml of diethyl ether are subsequently added. The reaction is now stopped by adding 30 ml of a saturated NaHCO$_3$ solution. Extraction is effected 3 times with 50 ml each time of Et$_2$O, and the combined organic phases are dried over Na$_2$SO$_4$. After removing the solvents on a rotary evaporator, 9.0 g of an brown-coloured oil are obtained. This is purified by column chromatography (380 9 of SiO$_2$, 4:1 heptane/ethyl acetate) to obtain 3.0 g of a dark orange-coloured crystalline product. Yield: 3.0 g, 42% of theory.

$^1$H NMR (300.13 MHz, CDCl$_{36}$): δ0.85 (d, 3 H, HCH$_3$), 0.95 (d, 3 H, HCH$_3$), 1.60 (m, 1 H, CH(CH$_3$)$_2$), 3.40 (br. s, 1 H, Cp-H), 3.70 (m, 1 H, O—CH$_2$—CH—), 3.95 (m, 1 H, O—CH$_2$—CH—), 4.15 (6 H, Cp-H ), 4.40 (m, 1 H, O—CH$_2$—CH—), 4.95 (m, 1 H, Cp-H), 7.60 (m, 2 Ar—H), 7.75 (m, 1 H, Cp-H), 7.90 (m, 3 H, Cp-H). $^{31}$P{$^1$H} (121.5 MHz, CDCl$_3$): δ−15.2.

Procedure for the Experiments:

All reactions were carried out using Schlenk technology and under protective gas atmosphere.

General Hydrogenation:

After an appropriate pre-treatment, the particular catalyst solution is transferred to the inertized 50 ml mini-autoclave (inject argon and decompress 3×), and the starting material (substrate) and the base are subsequently added. Afterwards, the autoclave is sealed and hydrogen is injected to the desired pressure. The reaction is started by switching on the magnetic stirrer. When the hydrogenation time has elapsed, the magnetic stirrer is switched off and the autoclave is ventilated. A sample for the GC analysis is taken to determine yield and conversion.

Determination of the Conversion and of the ee Value:

Conversion and ee value are determined on these substrates in one analysis step.

Column: Beta-Dex 110 (30 m); 110° C. isothermal; 100 k Pa of H$_2$ as carrier gas;

Reactant 1=5.6 min; E1=7.7 min; E2=8.1 min.
Reactant 5=8.8 min, E1=12.5 min; E2=13.0 min.
Reactant 7=6.2 min; E1=8.4 min; E2=8.8 min.

Column: Beta-Dex 110 (30 m); 110° C. isothermal; 120 k Pa of H$_2$ as carrier gas;

Reactant 4=23.4 min; E1=25.7 min; E2=26.7 min.
Reactant 6=7.3 min; E1=13.6 min; E2=14.3 min.

Column: Beta-Dex 110 (30 m); 130° C. isothermal; 100 k Pa of H$_2$ as carrier gas;

Reactant 2=5.7 min, E1=9.5 min; E2=10.9 min.
Reactant 3=7.7 min, E1=11.1 min; E2=11.7 min.
Results Details of the experiments 1 to 65 with regard to the reactants used, reaction conditions and the results achieved are listed in the following Table 1:

TABLE 1

| Experiment | Ligand | Substrate | P(H₂) [bar] | S/C | Time [h] | Yield [%] | ee [%] |
|---|---|---|---|---|---|---|---|
| 1 | A | 1 | none | 200 | 20 | 96 | 89.0 |
| 2 | A | 1 | 1.1 | 200 | 20 | 98 | 99.0 |
| 3 | A | 1 | 80 | 200 | 1 | 99 | 98.1 |
| 4 | B | 1 | 80 | 200 | 1 | 99 | −98.3 |
| 5 | C | 1 | 80 | 200 | 1 | 98 | 95.8 |
| 6 | D | 1 | 80 | 200 | 1 | 99 | 98.5 |
| 7 | E | 1 | 80 | 200 | 1 | 98 | 97.2 |
| 8 | F | 1 | 80 | 200 | 1 | 99 | 95.0 |
| 9 | G | 1 | 80 | 200 | 1 | 96 | 92.9 |
| 10 | H | 1 | 80 | 200 | 1 | 89 | 96.9 |
| 11 | I | 1 | 80 | 200 | 1 | 77 | 93.0 |
| 12 | J | 1 | 80 | 200 | 1 | 77 | 86.7 |
| 13 | K | 1 | 80 | 200 | 1 | 56 | 96.1 |
| 14 | A | 2 | 80 | 200 | 1 | 99 | 94.7 |
| 15 | B | 2 | 80 | 200 | 1 | 99 | −90.4 |
| 16 | C | 2 | 80 | 200 | 1 | 99 | 93.6 |
| 17 | D | 2 | 80 | 200 | 1 | 99 | 92.9 |
| 18 | E | 2 | 80 | 200 | 1 | 99 | 90.2 |
| 19 | F | 2 | 80 | 200 | 1 | 99 | 94.3 |
| 20 | G | 2 | 80 | 200 | 1 | 97 | 93.2 |
| 21 | H | 2 | 80 | 200 | 1 | 76 | 90.7 |
| 22 | I | 2 | 80 | 200 | 1 | 61 | 82.3 |
| 23 | J | 2 | 80 | 200 | 1 | 57 | 72.6 |
| 24 | K | 2 | 80 | 200 | 1 | 48 | 76.8 |
| 25 | A | 3 | 80 | 200 | 1 | 99 | 95.8 |
| 26 | B | 3 | 80 | 200 | 1 | 96 | −96.9 |
| 27 | C | 3 | 80 | 200 | 1 | 98 | 94.9 |
| 28 | D | 3 | 80 | 200 | 1 | 97 | 96.6 |
| 29 | E | 3 | 80 | 200 | 1 | 98 | 96.4 |
| 30 | F | 3 | 80 | 200 | 1 | 98 | 94.1 |
| 31 | G | 3 | 80 | 200 | 1 | 98 | 91.9 |
| 32 | H | 3 | 80 | 200 | 1 | 80 | 95.0 |
| 33 | I | 3 | 80 | 200 | 1 | 72 | 89.5 |
| 34 | J | 3 | 80 | 200 | 1 | 67 | 36.7 |
| 35 | K | 3 | 80 | 200 | 1 | 55 | 89.8 |
| 36 | A | 4 | 80 | 200 | 1 | 98 | 95.0 |
| 37 | B | 4 | 80 | 200 | 1 | 97 | −95.3 |
| 38 | C | 4 | 80 | 200 | 1 | 95 | 95.6 |
| 39 | D | 4 | 80 | 200 | 1 | 86 | 97.5 |
| 40 | E | 4 | 80 | 200 | 1 | 98 | 95.7 |
| 41 | F | 4 | 80 | 200 | 1 | 70 | 84.4 |
| 42 | G | 4 | 80 | 200 | 1 | 43 | 88.4 |
| 43 | H | 4 | 80 | 200 | 1 | 51 | 95.3 |
| 44 | I | 4 | 80 | 200 | 1 | 28 | 90.7 |
| 45 | J | 4 | 80 | 200 | 1 | 63 | 82.4 |
| 46 | K | 4 | 80 | 200 | 1 | 27 | 95.4 |
| 47 | A | 5 | 80 | 200 | 1 | 99 | 98.4 |
| 48 | B | 5 | 80 | 200 | 1 | 97 | −95.7 |
| 49 | C | 5 | 80 | 200 | 1 | 100 | 98.3 |
| 50 | D | 5 | 80 | 200 | 1 | 80 | 99.3 |
| 51 | E | 5 | 80 | 200 | 1 | 98 | 98.0 |
| 52 | F | 5 | 80 | 200 | 1 | 94 | 96.2 |
| 53 | G | 5 | 80 | 200 | 1 | 80 | 93.7 |
| 54 | H | 5 | 80 | 200 | 1 | 56 | 96.2 |
| 55 | I | 5 | 80 | 200 | 1 | 45 | 95.1 |
| 56 | J | 5 | 80 | 200 | 1 | 48 | 91.6 |
| 57 | K | 5 | 80 | 200 | 1 | 14 | 94.1 |
| 58 | A | 6 | 80 | 200 | 42 | 86 | 97.2 |
| 59 | A | 7 | 80 | 200 | 1 | 10 | 93.9 |
| 60 | A | 1 | 80 | 10 000 | 1 | 98 | 98.5 |
| 61 | A | 1 | 80 | 50 000 | 78 | 99 | 99.0 |
| 62 | A | 1 | 80 | 10 000 | 6 | 98 | 98.5 |
| 63 | A | 3 | 20 | 20 000 | 1 | 92 | 96.2 |
| 64 | E | 3 | 20 | 20 000 | 1 | 92 | 95.5 |
| 65 | E | 3 | 20 | 20 000 | 1.5 | 99 | 97.5 |

Experiments 1 and 2: These are carried out under typical transfer hydrogenation conditions. To 10 ml of isopropanol are added: 0.005 mmol of [RuCl₂(PPh₃)(A)], 1 mmol of the substrate 1 and 0.025 mmol of PrOK as a base. The reaction is carried out at room temperature under argon in experiment 1 and at a hydrogen pressure of 1.1 bar in experiment 2.

Experiments 3 to 59: The particular catalyst is prepared "in situ" by allowing 0.1 mmol of ligand and 0.1 ml of [RuCl₂(PPh₃)₃] in 20 ml of toluene to react for one hour under reflux conditions. 2 ml of the resulting solution are then added to 2 mmol of the substrate which is in a 20 ml flask. 1 ml of a 1 molar aqueous solution of NaOH is then added and the flask is placed in a multiparallel autoclave. Hydrogen is then injected to a pressure of 80 bar for one hour (unless stated otherwise, see table).

Experiments 60 to 62: A Schlenk flask is charged with 0.005 mmol of [RuCl₂(PPh₃)(A)], 50 mmol of substrate and 18 ml of toluene in experiment 60, or 250 mmol of substrate and 2 ml of toluene in experiment 61, and 1 ml of a 1 molar aqueous solution of NaOH. The compositions are placed in 50 ml autoclave and subjected to a hydrogen pressure of 80 bar for one hour in experiment 60, and for 78 hours in experiment 61. For reaction 62, the same reaction conditions were used as for 60 except that the reaction was conducted as "neat", namely without addition of toluene.

Experiments 63 to 65: A Schlenk flask is charged with 0.005 mmol of [RuCl₂(PPh₃)₃], 0.005 mmol of ligand and 9 ml of toluene and kept under reflux conditions for one hour. 100 mmol of the substrate and 1 ml of a 1 molar aqueous solution of NaOH are then added at room temperature to the catalyst prepared "in situ". The compositions are placed in a 50 ml autoclave and subjected to a hydrogen pressure of 20 bar for one or one and a half hours (see table).

Discussion of the Results

The first two comparative experiments which were carried out under the typical conditions of the transfer hydrogenation show that the application of a hydrogen pressure of 1.1 bar has little influence on the activity but enables higher enantioselectivity. This interesting and important result shows that the hydrogenation with hydrogen enables one of the major disadvantages of the transfer hydrogenation to be avoided, i.e. the decrease in the percentage enantioselectivity with increasing time (which approaches the equilibrium). It was also possible to show that for hydrogenations under elevated pressure of 20 to 80 bar, in the presence of an organic solvent such as toluene instead of isopropanol, turnover numbers of up to 50 000 can be achieved. It is also remarkable that a substrate such as isobutyrophenone (substrate 6) which is known to be difficult to hydrogenate can be hydrogenated under comparable conditions with high enantioselectivity (ee=97.2%).

Hydrogenation of imines (substrate 8):

TABLE 2

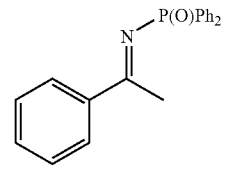

| Experiment | Ligand | Substrate | P(H₂) [bar] | S/C | Time [h] | Yield [%] | ee [%] |
|---|---|---|---|---|---|---|---|
| 66 | A | 8 | 80 | 50 | 16 | 15 | 90 |
| 67 | J | 8 | 80 | 50 | 16 | 14 | 91 |

Experiments 66 and 67: The particular catalyst is prepared "in situ" by allowing 0.1 mmol of ligand and 0.1 ml of [RuCl$_2$(PPh$_3$)$_3$] in 20 ml of toluene to react for one hour under reflux conditions. 2 ml of the resulting solution are then added to 2 mmol of the substrate which is in a 20 ml flask. 1 ml of a 1 molar aqueous solution of NaOH is then added and the flask is placed in a multiparallel autoclave. Hydrogen is then injected to a pressure of 80 bar for 16 hours. The results are listed in table 2 above.

Discussion of the Results:

It is interesting to note that even with difficult hydrogenation substrates such as imines, the hydrogenation proceeds following analogous conditions to the one described with ketones. Remarkable enantiomeric excesses higher than 90% ee can be achieved.

The invention claimed is:

1. A process for hydrogenating a substrate containing a carbon-heteroatom double bond, which includes the step of reacting the substrate with hydrogen gas in the presence of a hydrogenation catalyst and of a base, wherein the hydrogenation catalyst is a transition metal complex of the formula (I)

[X Y Ru (P R$_1$R$_2$R$_3$) (P-Z-N)]     (I)

where

X, Y are each independently a hydrogen atom, halogen atom, C$_{1-8}$alkoxy or C$_{1-8}$acyloxy group, or a coordinatively bound organic solvent molecule containing at least one heteroatom having at least one free electron pair, in which case the charge of the resulting cationic complex is balanced by an anion, R$_1$, R$_2$, R$_3$ are each independently an alkyl, alkyloxy, alkylthio, dialkylamino, cycloalkyl, cycloalkyloxy, cycloalkylthio, dicycloalkylamino, aryl, aryloxy, arylthio or diarylamino group, said groups being unsubstitued or substituted by 1,2 or 3 radicals which are each independently selected from C$_{1-4}$alkyl groups and C$_{1-4}$alkoxy groups, or one of the R$_1$, R$_2$, R$_3$ radicals is as defined above and the remaining 2 radicals which, linked either via an oxygen bridge or directly to the phosphorus atom, form, including the phosphorus atom, an unsubstituted or substituted 4- to 8-membered ring, P-Z-N is a bidentate ligand which contains an sp$^2$-hybridized nitrogen atom and is of the formula (II)

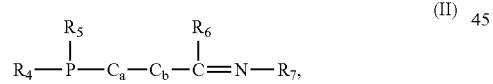

wherein

R$_4$, R$_5$ are each independently a linear, branched or cyclic unsubstituted or substituted C$_{1-8}$alkyl or C$_{2-8}$alkenyl group; unsubstituted or substituted C$_{6-18}$aryl, C$_{3-18}$heteroaryl, C$_{3-8}$cycloalkyl, (C$_{1-8}$Alkyl)$_{1-3}$-(Hetero)Aryl, whereby possible substituents are halogen, organohalogen group, O(C$_{1-8}$)alkyl, N(C$_{1-8}$alkyl)$_2$; or R$_4$ and R$_5$ together are a saturated or aromatic ring composed of 5 to 10 atoms including the phosphorus atom, C$_a$, C$_b$ are each a part of an unsubstituted or substituted (hetero)aryl having at least 6 π-electrons, R$_6$ is a hydrogen atom, a linear, branched or cyclic unsubstituted or substituted C$_{1-10}$alkyl or C$_{2-10}$alkenyl group, an unsubstituted or substituted aromatic ring, a —OR$_{6'}$ or —NR$_{6'}$R$_{6''}$ radical, wherein R$_{6'}$ and R$_{6''}$ are as defined for R$_6$, R$_7$ is a hydrogen atom, a linear, branched or cyclic C$_{1-10}$alkyl or C$_{2-10}$alkenyl group, or an R$_{7'}$CO or R$_{7'}$SO$_2$ radical where R$_{7'}$ is a C$_{1-8}$alkyl or aryl group, or R$_6$ and R$_7$ together are an unsaturated (hetero)cycle composed of unsubstituted or substituted 5 to 10 ring atoms, including the carbon and the nitrogen atom to which R$_6$ and R$_7$ are bonded, and including or not including further heteroatoms, whereby said substrate to be hydrogenated is a prochiral monocyclic or polycyclic aryl ketone or heteroary ketone, optionally substituted by linear or branched C$_{1-8}$alkyl, C$_{1-8}$alkoxy group, or halogen atoms.

2. A process according to claim 1, wherein X, Y in the formula (I) are each independently a hydrogen atom or a halogen atom.

3. A process according to claim 2, wherein X, Y in the formula (I) are each a halogen atom.

4. A process according to claim 1, wherein R$_1$, R$_2$, R$_3$ in the formula (I) are each independently a methyl, ethyl, propyl, i-propyl, n-butyl, i-butyl, sec-butyl, tert-butyl, cyclopentyl, cyclohexyl, phenyl, o- or p-tolyl, p-isopropylphenyl or mesityl group.

5. A process according to claim 1, wherein R$_4$, R$_5$ in the formula (I) are each independently a radical selected from methyl, ethyl, n-propyl, i-propyl, n-butyl, i-butyl, cyclohexyl, phenyl, o- or p-tolyl, mesityl, α- or β-naphthyl.

6. A process according to claim 1, wherein C$_a$, C$_b$ in the formula (II) are part of a pure 6 π-electron system in the form of Unsubstituted or substituted benzene or in the form of an Unsubstituted or substituted cyclopentadienide ion as a ligand of a metallocene.

7. A process according to claim 1, wherein R$_6$ and R$_7$ in the formula (II) together are an unsaturated heterocycle composed of unsubstituted or substituted 5 to 10 ring atoms, including the carbon and the nitrogen atom to which R$_6$ and R$_7$ are bonded, and including or not including further heteroatoms.

8. A process according to claim 1, wherein the ligand of the formula (II) is a ligand of the general formula (IIb)

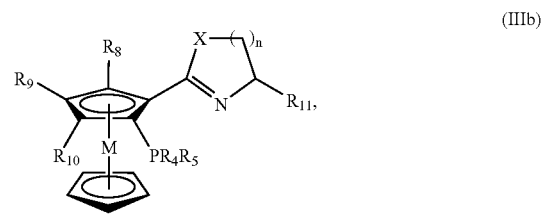

wherein n=1 or 2,

M=Fe, Ru or Os,

X=O, S or N,

R$_4$, R$_5$ are each radicals corresponding to the definition given under formula (II), R$_{11}$ is a C$_{2-8}$alkoxyalkyl, C$_{7-19}$aralkyl, C$_{3-18}$heteroaryl, C$_{4-19}$heteroaralkyl, (C$_{1-8}$alkyl)$_{1-3}$—C$_{6-18}$(hetero)aryl, (C$_{1-8}$alkyl)$_{6-18}$cycloalkyl, C$_{3-8}$cycloalkyl, C$_{3-8}$cycloalkyl-C$_{1-8}$alkyl, C$_{1-8}$alkyl or C$_{6-18}$aryl radical, R$_{8,9,10}$ are each independently a C$_{1-8}$alkyl, C$_{2-8}$alkoxyalkyl, C$_{6-18}$aryl, C$_{7-19}$aralkyl, C$_{3-18}$heteroaryl, C$_{4-19}$heteroaralkyl, (C$_{1-8}$alkyl)$_{1-3}$-C$_{6-18}$(hetero)aryl, C$_{3-8}$cycloalkyl, (C$_{1-8}$alkyl)$_{1-3}$-C$_{6-18}$cycloalky or C$_{3-8}$cycloalkyl-C$_{1-8}$alkyl radical, or H.

9. A process according to claim 8, wherein the ligand of the formula (IIIb) is selected from the ligands A to G:

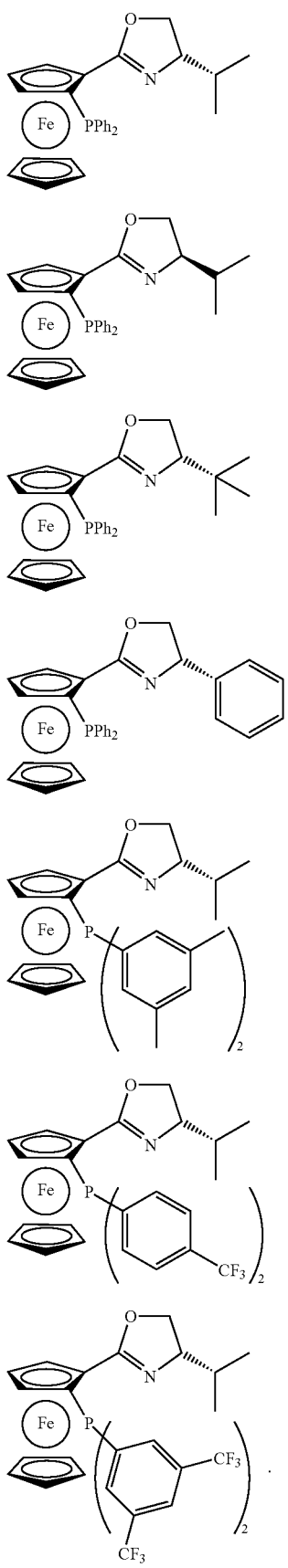

A

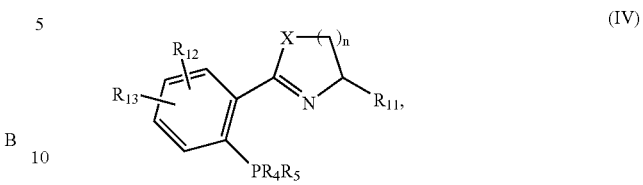

10. A process according to claim 1, wherein the ligand of the formula (II) is a ligand of the general formula (IV)

wherein
n = 1 or 2,
X = O, S or N,
$R_4$, $R_5$ are each radicals corresponding to the definition given under formula (II),
$R_{11}$ is a $C_{2-8}$alkoxyalkyl, $C_{7-19}$aralkyl, $C_{3-18}$heteroaryl, $C_{4-19}$heteroaralkyl,
$(C_{1-8}$alkyl$)_{1-3}$-$C_{6-18}$(hetero)aryl, $(C_{1-8}$alkyl$)_{1-3}$-$C_{6-18}$cycloalkyl, $C_{3-8}$cycloalkyl,
$C_{3-8}$cycloalkyl-$C_{1-8}$alkyl, $C_{1-8}$alkyl or $C_{6-18}$aryl radical,
$R_{12}$, $R_{13}$ are each independently a $C_{1-8}$alkyl or $C_{1-4}$alkoxy radical, or H, or are together a fused cycloalkyl or aryl ring.

11. A process according to claim 10, wherein the ligand of the formula (IV) corresponds to the formula J:

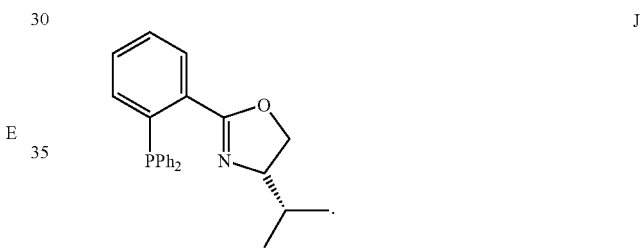

12. A process according to claim 1, wherein the ligand of the formula (II) is a ligand of the general formula (V)

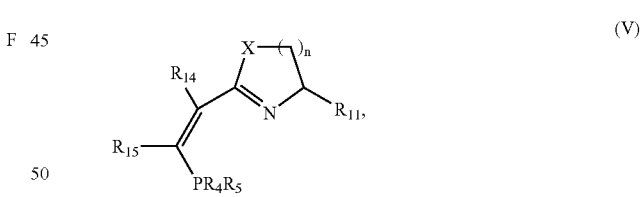

wherein
= 1 or 2,
X = O, S or N,
$R_4$, $R_5$ are each radicals corresponding to the definition given under formula (II),
$R_{11}$ is a $C_{2-8}$alkoxyalkyl, $C_{7-19}$aralkyl, $C_{3-18}$heteroary, $C_{4-19}$heteroaralkyl
$(C_{1-8}$alkyl$)_{1-3}$-$C_{6-18}$(hetero)aryl, $(C_{1-18}$ alkyl$)_{1-3}$-$C_{6-18}$cycloalkyl, $C_{3-8}$cycloalkyl,
$C_{3-8}$cycloalkyl-$C_{1-8}$alkyl, $C_{1-8}$alkyl or $C_{6-18}$aryl radical, and
$R_{14}$ and $R_{15}$ together are a 6 π- or 10 π-electron heteroaromatic system, unsubstituted or substituted by linear or branched $C_{1-8}$alkyl radicals, and possible heteroatoms are N, O, or S.

13. A process according to claim 12, wherein the ligand of the formula (V) corresponds to one of the formulae H, I and K:

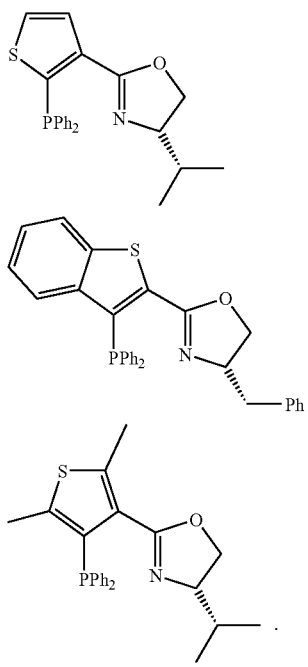

14. A process according to claim 1, wherein the substrate to be hydrogenated is selected from one of ketones 1 to 7:

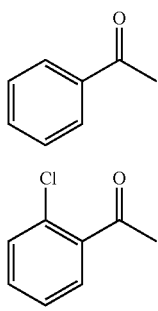

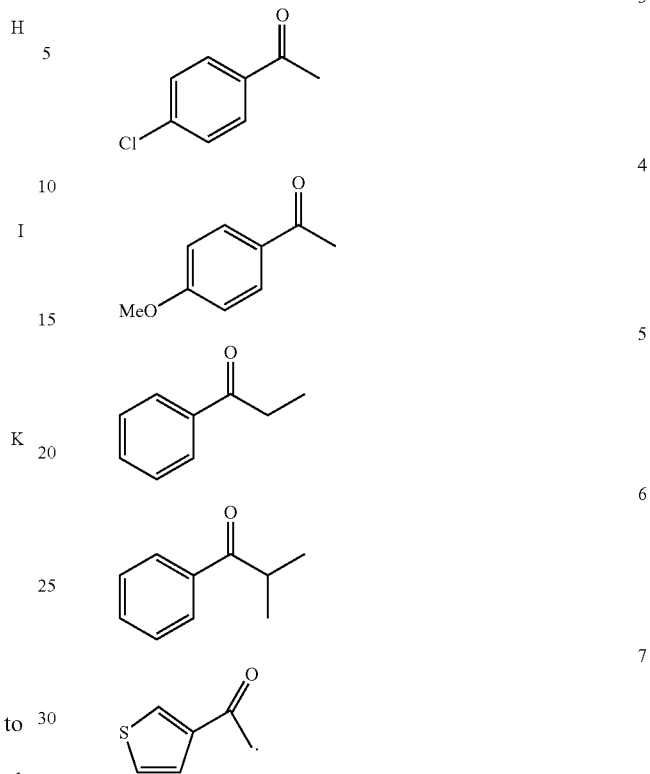

15. A process according to claim 3, wherein said halogen atom is chlorine.

16. A process according to claim 8, wherein n =1, M =Fe, and X=O.

17. A process according to claim 10, wherein n =1, and X =O.

18. A process according to claim 10, wherein n =1, and X =O.

* * * * *